United States Patent [19]

Wake et al.

[11] 4,302,675

[45] Nov. 24, 1981

[54] METHOD OF MULTIPLANAR EMISSION TOMOGRAPHY AND APPARATUS THEREFOR

[75] Inventors: Robert H. Wake, Solon; Stephen C. Gottschalk, Macedonia; Kendall A. Smith, South Russel, all of Ohio

[73] Assignee: Technicare Corporation, Solon, Ohio

[21] Appl. No.: 113,871

[22] Filed: Jan. 21, 1980

[51] Int. Cl.³ .......................... G01T 1/20; G21F 5/04
[52] U.S. Cl. .................................. 250/363 S; 250/511
[58] Field of Search ................... 250/360, 363 S, 366, 250/367, 369, 445 T, 505, 511, 513

[56] References Cited

U.S. PATENT DOCUMENTS

```
3,011,057  11/1961  Anger.
3,612,865  10/1971  Walker.
4,181,839   1/1980  Hatton et al. ................ 250/363 S
4,197,460   4/1980  Anger ........................... 250/363 S
```

OTHER PUBLICATIONS

Kuhl et al., "Image Separation Radioisotope Scanning" Radiology, vol. 80, 1963, pp. 653-662.
Gilbert, "Herative Methods for the Three-Dimensional Reconstruction of an Object from Projections" J. Theor. Biol. vol. 36, 1972, pp. 105-117.
Vogel et al., "A New Method of Multiplanar Emission Tomography using a Seven Pinhole Collimator and an Anger Scintillation Camera" Journal of Nuc. Medicine, vol. 19, No. 6, 1978, pp. 648-654.

Primary Examiner—Davis L. Willis
Assistant Examiner—Janice A. Howell
Attorney, Agent, or Firm—Michael A. Kaufman

[57] ABSTRACT

A method of emission tomography using a gamma camera and a rotating collimator having an array of a large number of slanted, small diameter holes. A planar projection corresponding to each angular orientation assumed by the collimator is recorded. From these series of planar projections, a three-dimensional simulation model is reconstructed by an iterative algorithm which approximates the emitting object. The simulated model comprises multiple separable planes.

13 Claims, 6 Drawing Figures

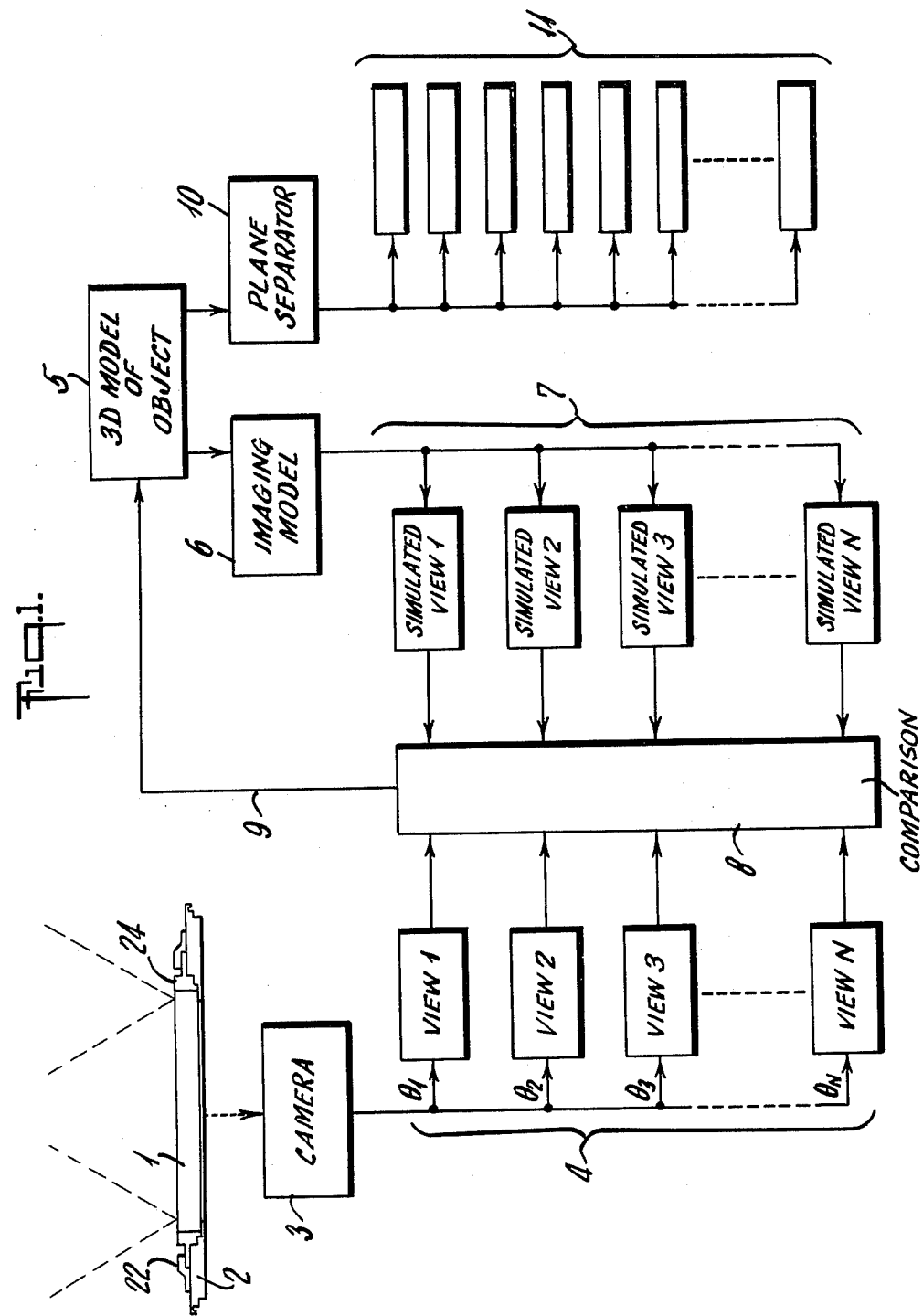

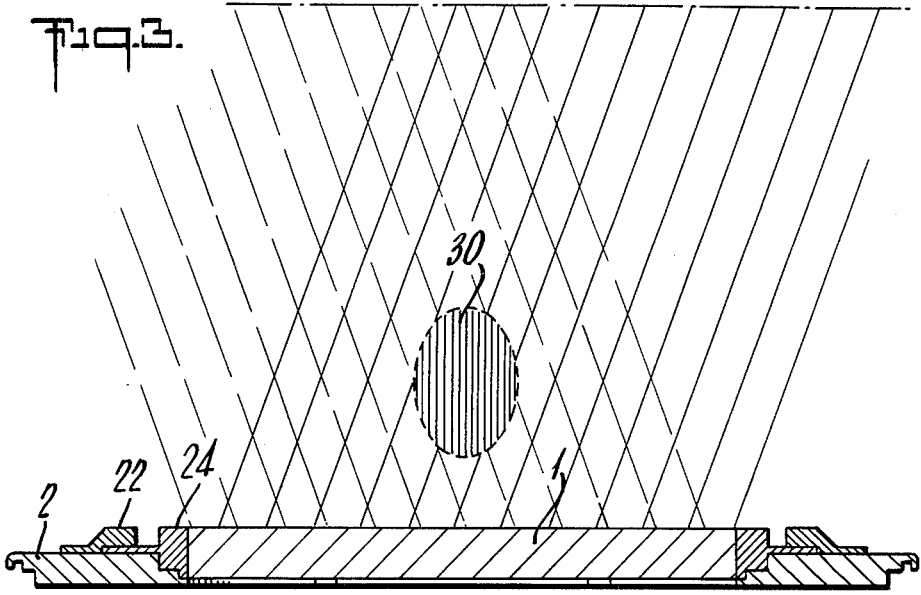
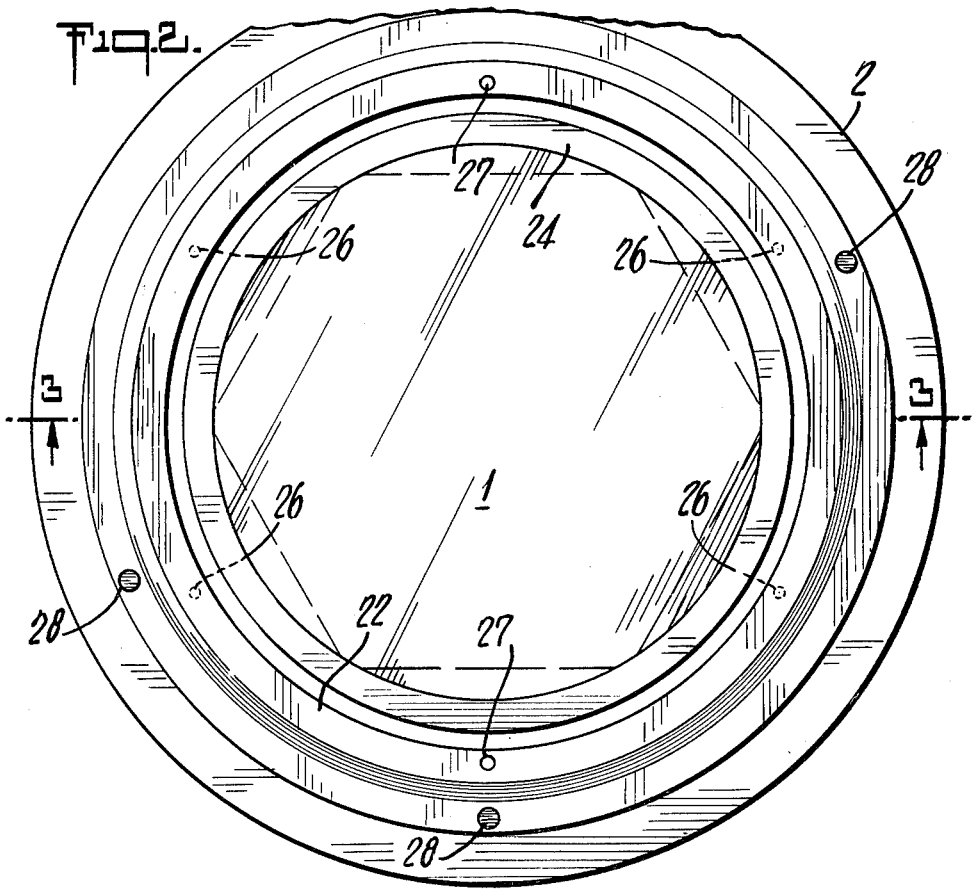

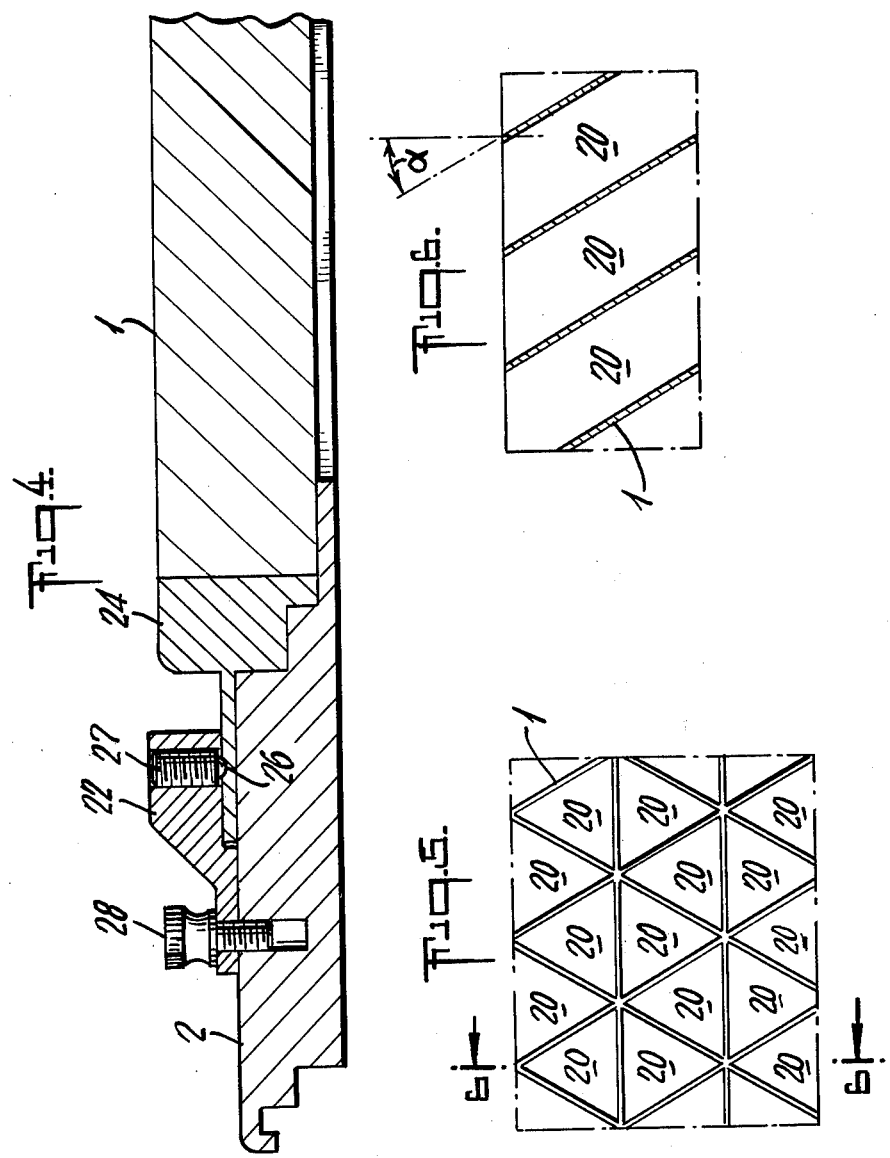

METHOD OF MULTIPLANAR EMISSION TOMOGRAPHY AND APPARATUS THEREFOR

TECHNICAL FIELD

This invention relates to multiplanar tomography in nuclear medicine. An apparatus and method are disclosed for reconstructing a three-dimensional distribution of radioisotopes in a volume of interest utilizing a gamma camera and a rotating collimator in which the holes are slanted relative to the facial plane of the camera.

BACKGROUND ART

Conventional nuclear medicine techniques produce an image depicting the distribution of radioactive compounds within organs of the human body by filtering the high energy photons or gamma rays emitted by those compounds by means of a "collimator." Conventional collimators typically have a thickness of radiation absorbent material punctuated by a large number of parallel, relatively small diameter holes. These holes are of such small diameter compared to the thickness of the collimator that only those photons that enter the holes at the angle of the hole can pass therethrough. The holes of such conventional collimators are typically perpendicular to the plane of their faces. A photon that passes through the collimator produces a flash of light as it strikes a scintillation crystal located behind the collimator. Each such strike is amplified by a photomultiplier to generate a detectable signal. The pattern of these flashes represents the distribution of radioisotope aligned directly in front of each of the holes. The image generated from the processing of a great many of such signals is a two-dimensional projection of a three-dimensional distribution as a conventional X-ray photograph is a two-dimensional projection of a three-dimensional volume of interest. Such two-dimensional images of radioisotope distribution may be achieved by the well-known scintillation camera, also called the Anger camera after its inventor, and described in U.S. Pat. No. 3,011,057.

It is often important to the interpretation of nuclear medicine studies to understand the actual three-dimensional distribution of isotope within the organ being studied. In a conventional nuclear medicine imaging technique, however, one spatial dimension of information is lost each time as image is produced. Though images can be produced from various viewing angles and the resulting pictures considered together, it is often difficult to combine these various views into an understanding of the actual three-dimensional distribution.

Several techniques have been utilized in an attempt to produce three-dimensional "image" of isotope distribution within an organ.

Earlier techniques included moving the patient and/or detector so that radioactivity from other than a single depth is "blurred". One such method is disclosed in U.S. Pat. No. 3,612,865 to Walker. No actual removal of out-of-plane activity occurs, but rather such information is spread out in the image so that any information distant from the plane of interest becomes less pronounced. However, there appears a high background activity in the resulting image. The depth where the blurring is minimized is varied by adjusting the processing circuits. Multiple images may be produced, each emphasizing a different depth.

Other techniques rely on a focusing technique to increase collimator sensitivity at a certain depth. Several techniques for achieving depth discrimination using rectilinear scanning including inclining the detectors is disclosed in Kuhl, et al., "Image separation Radioisotope Scanning" 80 Radiology (1963) 653.

More recent work has begun to utilize various reconstruction techniques to separate data from multiple views into separate planes, each representing the isotope distribution at a specific depth from the front of the detector.

Several reconstruction methods to generate a three-dimensional density distribution are discussed in Gilbert, P., "Iterative Methods for the Three-dimensional Reconstruction of an Object from Projections," 36 J. Theor. Biol. (1972) 105. Gilbert discusses and compares several iterative reconstruction methods including the Algebraic Reconstruction Technique (ART) and the Simultaneous Iterative Reconstruction Technique (SIRT).

Various techniques have been used to produce multiple views and to optimize the information obtained from them. These include various types of coded apertures, freznel zone plates, and multiple overlapping pinholes. All of these techniques have performed well with limited source distributions, but background activity and extended sources have limited the quality of the images.

A recent development is the seven pinhole, non-overlapping images technique described by Vogel et al., 19 *Journal of Nuclear Medicine* (1978) 648. Seven independent projections are produced simultaneously, through seven pinholes, each viewing a common volume directly in front of the collimator. The seven images are processed by a reconstruction technique to yield multiple planar images, each representing a slice through the common volume. This technique has shown improved detection sensitivity in comparison with conventional collimators.

SUMMARY OF THE INVENTION

Applicants have discovered a method of multiplanar emission tomography with specific application in nuclear medicine and in particular for cardiac studies. Applicants have further discovered an apparatus for carrying out multiplanar imaging using a planar detector such as a scintillation camera in combination with a rotatable collimator having a tightly packed array of a multiplicity of apertures extending through the collimator at an angle relative to the plane of the detector.

In a preferred embodiment, the apparatus for producing a multiplanar representation of a radioisotope distribution within a volume of interest comprises a rotatable collimator having a multiplicity of apertures to permit the passage of photons therethrough, wherein the apertures are slanted relative to the axis of rotation of the collimator. The apparatus further comprises a planar imaging device disposed adjacent the collimator for detecting the photons passing through the apertures of the collimator from the volume of interest, means for recording a plurality of projections of the volume of interest, each projection acquired from the photons detected by the imaging device during an associated angular orientation assumed by the rotated collimator, reconstruction means for generating a three dimensional array from the plurality of projections, wherein the three dimensional array is a simulation of the radioisotope distribution within the volume of interest, and means for separating the three dimensional array into a plurality of discrete planar sections, each section representing a planar section of the volume of interest.

In a preferred embodiment the method of multiplanar emission tomography comprises directing a collimator having a multiplicity of apertures toward a photon emitting volume of interest having a radioisotope distribution, acquiring photons from the emitting volume of interest by a detector positioned adjacent the collimator such that the collimator is interposed between the detector and the volume of interest, rotating the collimator during photon acquisition to record a plurality of projections each corresponding to an angular orientation of the collimator; and reconstructing a three dimensional array of the radioisotope distribution within the volume of interest by comparison with the plurality of projections, the array being separable into multiple planes of predetermined width, each such plane representing a planar section of the volume of interest.

BRIEF DESCRIPTION OF THE DRAWINGS

FIG. 1 is a schematic block diagram of the multiplanar emission tomography according to the present invention including rotatable collimator and imaging device;

FIG. 2 is a plan view of a rotatable collimator and mounting fixture therefor;

FIG. 3 is a section of FIG. 2 taken along line 3—3 showing a volume of interest viewable through the collimator;

FIG. 4 shows a detail of the collimator and fixture of FIG. 2 on an enlarged scale;

FIG. 5 is a sectional detail of the apertures of the collimator of FIG. 2;

FIG. 6 is a section of FIG. 5 taken along line 6—6 illustrating the slant of the apertures of FIG. 5.

BEST MODE FOR CARRYING OUT THE INVENTION

FIG. 1 shows a section of a collimator 1 retained by a fixture or mount 2 and positioned adjacent a planar imaging device such as a scintillation camera 3, typically an Anger gamma ray camera. The collimator 1 is shown in greater detail in FIGS. 2 and 3. Collimator 1 is made of lead or other radiation opaque material. The lead collimator 1 has a multiplicity of holes or apertures 20 extending through its thickness.

Holes 20, shown in detail in FIG. 5, are normally parallel to each other although diverging or converging orientations can be used. The holes 20 are generally distributed evenly over the area of the collimator 1 although an uneven distribution or uneven hole sizes or shapes are suitable for special cases. In a preferred embodiment, the holes 20 are triangular in cross section, though they may be generally cylindrical. The holes 20 are generally aligned at an angle $\alpha$ relative to the normal direction as shown in FIG. 6 nonperpendicular to the face of the scintillation camera 3.

The collimator 1 is mounted in front of and parallel to the face or crystal of the scintillation camera 3 in the fixture or mount 2. The fixture 2 permits the collimator 1 to be rotated in a plane parallel to the camera crystal. Rotation can be manual or motorized.

The fixture 2 is shown in enlarged scale in FIG. 4 includes locking mechanism 22 which engages collimator rim 24 to permit collimator 1 to sequentially assume predetermined angular orientations. The locking mechanism 22 is further provided with detent button 26 which secures the collimator rim 24 by engaging detents 27 therein located at intervals corresponding to the predetermined angular orientations of the collimator 1. The level of engagement of collimator rim 24 by locking mechanism 22 is made adjustable by a set screw 28.

Alternatively, the collimator 1 can be allowed to rotate continuously during the image recording process.

In practice, the camera 3 is directed toward a volume of interest 30, the object to be imaged and a separate image 4 is recorded for each view 1 through N of the preset angular orientation of the collimator 1. Each image, or each gamma ray recorded must also have recorded the associated angular orientation of the collimator 1. Recording the gamma rays during continuous rotation results, in effect, in a very large set of separate images each representing an angular orientation that the collimator 1 passes through during its rotation. Alternatively, the collimator could be tilted such that the viewing angle is varied discretely or continuously during the image recording process.

Each of the resulting images 4 provides a conventional two dimensional representation of the radioisotope distribution in front of the camera-collimator. Because of the nonperpendicular angle $\alpha$ of the holes 20 in the collimator 1, each image depicts the volume 30 as viewed from a different orientation.

From the multiples views 1–N, a three dimensional model 5 of the isotope distribution in the volume of interest 3 is generated. This model 5 is successively "imaged" by a simulation of the camera-collimator imaging model 6 and simulated images 7 are produced. These simulated images 7 are compared 8 with the actual images 4 produced by the camera-collimator. Discrepancies 9 are used to adjust the model 5 and the entire process is repeated. This iterative process is continued until a desired degree of accuracy is reached. The resulting model is then separated 10 into planes 11 representing different distances from the collimator.

Initially, three dimensional model 5 is a three dimensional array with random or no information. Then, based on a model 6, a simulated view 1 is generated which is assumed to contain the isotope distribution that would result in a projected or two dimensional view 1 at the angular orientation of collimator that corresponds to view 1. The two views are compared at 8 and iteratively corrected. The process occurs for all N views corresponding to the N angular orientations assumed by the collimator 1.

An iterative reconstruction technique is preferred, but alternate techniques could be used including 3-dimensional Fourier reconstruction, convolution and back-projection methods and matrix inversion methods.

Iterative techniques are preferred because they can easily incorporate a priori information, non-uniform attenuation, different imaging geometries, data noise and other sources of image degradation. The preferred iterative technique is the iterative least squares method. This method chooses the reconstructed volume whose simulated images minimize the total chi square between the original views and the simulated views. During the simulated image reconstruction, the imaging model 6 considers the attenuation of the gamma rays as they pass through the object 30 prior to detection. Statistical variations in the number of gamma rays detected at each point in the actual views 4 must be considered during their comparison with the simulated views 7. The adjustments made in the model 5 minimizes the propagation of noise. Consideration is given to gamma rays originating in volumes not viewed by all viewing orientations. A priori knowledge of the usual type of volume distribution is used in weighting the modifications to the volume model.

The inventive apparatus and method is particularly well adapted for cardiac studies since a typical small field of view collimator 1 of about 9.75" diameter and 1" thickness with holes 20 at 25° slant will satisfactorily image to a depth of about 25 cm. These dimensions permit multiplanar imaging of the heart in most patients.

An alternative embodiment for the collimator 1 is to divide the collimator into several sub-collimators, each oriented such that the volume viewed by the sub-collimators overlaps. This reduces the number of images that need to be recorded since each image would in fact contain multiple non-overlapping sub-images, each providing a different view of the same volume in front of the camera.

What is claimed is:

1. An apparatus for producing a multiplanar representation of a radioisotope distribution within a volume of interest comprising:
   (a) a planar imaging device disposed adjacent said volume of interest for detecting photons emitting from said volume of interest;
   (b) a rotatable collimator interposed between said planar imaging device and said volume of interest having a multiplicity of apertures to permit the passage of photons therethrough, said apertures being nonperpendicular in relation to the face of said planar imaging device;
   (c) means for successively recording a plurality of projections of said volume of interest, each projection acquired from the photons detected by said imaging device associated with an angular orientation assumed by the rotatable collimator;
   (d) reconstruction means for generating a three-dimensional array from said plurality of projections, said three-dimensional array simulating the radioisotope distribution within the volume of interest; and
   (e) means for separating said three-dimensional array into a plurality of discrete planar sections, each such planar section of the volume of interest representing the radioisotope distribution in a planar section of said volume of interest corresponding to a specific normal distance from the collimator, thus corresponding to a specific depth range within said volume of interest, such that the aggregate of said discrete planar sections represents in three dimensions the radioisotope distribution within said volume of interest.

2. An apparatus for producing a multiplanar representation of a radioisotope distribution within a volume of interest comprising:
   (a) a rotatable collimator having a multiplicity of apertures to permit the passage of photons therethrough, said apertures being slanted relative to the axis of rotation of the collimator;
   (b) a planar imaging device disposed adjacent said collimator for detecting the photons passing through said apertures from said volume of interest;
   (c) means for successively recording a plurality of projections of said volume of interest, each projection acquired from the photons detected by said imaging device during each angular orientation assumed by the rotated collimator;
   (d) reconstruction means for generating a three-dimensional array from said plurality of projections, said three-dimensional array simulating the radioisotope distribution within the volume of interest; and
   (e) means for separating said three-dimensional array into a plurality of discrete planar sections, each such planar section of the volume of interest representing the radioisotope distribution in a planar section of said volume of interest corresponding to a specific normal distance from the collimator, thus corresponding to a specific depth range within said volume of interest, such that the aggregate of said discrete planar sections represents in three dimensions the radioisotope distribution within said volume of interest.

3. An apparatus according to claim 2 further comprising means for rotating said collimator at predetermined intervals to preselected stationary angular orientations such that each projection acquired corresponds to each angular orientation.

4. An apparatus according to claim 3 wherein said preselected angular orientations assumed by said collimator are equiangular.

5. An apparatus according to claim 4 wherein the predetermined interval associated with each preselected angular orientation is generally equal in time.

6. An apparatus according to claim 2 further comprising means for continuously rotating said collimator while said plurality of projections are being recorded.

7. An apparatus according to claim 6 further comprising means for recording the angular orientation of the collimator associated with the detection of each photon.

8. An apparatus according to claim 2 wherein the angle of each aperture varies in relation to its location in the collimator.

9. An apparatus according to claim 8 wherein:
   (a) said apertures have a triangular cross section;
   (b) said planar imaging device is a nuclear gamma camera; and
   (c) six projections are recorded, each projection corresponding to a different equiangular orientation of said collimator.

10. An apparatus for producing a multiplanar representation of a radioisotope distribution within a body comprising:
    (a) a rotatable collimator having a multiplicity of apertures to permit the passage of protons therethrough, a first plurality of said apertures being aligned generally parallel to each other and at a predetermined angle to the axis of rotation of the collimator;
    (b) means for intermittently rotating said collimator at preselected time intervals to one of a plurality of predetermined angular orientations of the collimator;
    (c) a planar imaging device disposed adjacent said collimator and generally parallel to the axis of rotation of the collimator for detecting the photons passing through the angled apertures of the collimator;
    (d) means for recording a plurality of planar projections, each planar projection corresponding to an angular orientation assumed by the collimator, each planar projection resulting from the photons acquired while said collimator assumed the angular orientation associated therewith;

(e) means for generating from said plurality of planar projections, a three-dimensional array simulating the radioisotope distribution within the body;

(f) means for comparing the recorded planar projections with the simulated three-dimensional array and for iteratively correcting said simulated array until a predetermined degree of accuracy is achieved; and (g) means for separating said three-dimensional array into a plurality of planar sections each section representing a discrete depth section of the body.

11. A method of multiplanar emission tomography comprising:

(a) directing a collimator having a multiplicity of slanted apertures toward a photon emitting volume of interest having a radioisotope distribution;

(b) acquiring photons passing through said slanted apertures from the emitting volume of interest by a detector positioned adjacent said collimator such that that collimator is interposed between said detector and the volume of interest;

(c) rotating said collimator during photon acquisition to record a plurality of projections, each corresponding to a particular angular orientation of said collimator;

(d) reconstructing a simulated three-dimensional array of said radioisotope distribution within the volume of interest; and (e) iteratively correcting said simulated array by comparison with the recorded projections until the simulated array achieves a predetermined degree of accuracy.

12. A method according to claim 11 wherein said corrected three-dimensional array is separable into multiple planes of predetermined thickness, each such plane representing a planar depth section of the volume of interest.

13. A method according to claim 11 wherein said reconstruction is an iteration by least squares.

* * * * *